(12) United States Patent
Mukaide et al.

(10) Patent No.: US 9,046,467 B2
(45) Date of Patent: Jun. 2, 2015

(54) X-RAY IMAGING APPARATUS AND X-RAY IMAGING METHOD

(71) Applicant: CANON KABUSHIKI KAISHA, Tokyo (JP)

(72) Inventors: Taihei Mukaide, Atsugi (JP); Kazuhiro Takada, Kawasaki (JP); Kazunori Fukuda, Fujisawa (JP); Masatoshi Watanabe, Isehara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 13/936,286

(22) Filed: Jul. 8, 2013

(65) Prior Publication Data

US 2013/0294581 A1 Nov. 7, 2013

Related U.S. Application Data

(62) Division of application No. 13/125,877, filed as application No. PCT/JP2010/060151 on Jun. 9, 2010, now Pat. No. 8,509,382.

(30) Foreign Application Priority Data

Jun. 18, 2009 (JP) .................................. 2009-145511

(51) Int. Cl.
*G01N 23/06* (2006.01)
*A61B 6/00* (2006.01)
(Continued)

(52) U.S. Cl.
CPC ................ *G01N 23/04* (2013.01); *A61B 6/484* (2013.01); *A61B 6/4233* (2013.01); *A61B 6/06* (2013.01); *G21K 1/06* (2013.01); *A61B 6/032* (2013.01); *G21K 2207/005* (2013.01)

(58) Field of Classification Search
CPC .............................. G01N 23/043; G21K 1/025
USPC ............................................... 378/2–3, 62, 51
See application file for complete search history.

(56) References Cited

U.S. PATENT DOCUMENTS

| 4,890,310 A | 12/1989 | Umetani et al. ................ 378/82 |
| 5,684,851 A | 11/1997 | Kurbatov et al. ............... 378/87 |

(Continued)

FOREIGN PATENT DOCUMENTS

| CN | 101257851 A | 9/2008 |
| CN | 101978257 A | 2/2011 |

(Continued)

OTHER PUBLICATIONS

Office Action issued Jul. 19, 2013 in counterpart Chinese Patent Application No. 201080026082.7, with translation.

(Continued)

*Primary Examiner* — Hoon Song
(74) *Attorney, Agent, or Firm* — Fitzpatrick, Cella, Harper & Scinto

(57) ABSTRACT

The invention is aimed to provide an X-ray imaging apparatus and the like ensuring a sufficient range of detecting the amount of X-ray movement with respect to the pixel size of a detector in comparison with the method disclosed in International Publication No. WO2008/029107. The X-ray imaging apparatus of the present invention has a splitting element which spatially linearly splits an X-ray beam; and a shielding unit which shields a part of the X-ray beam which is split by the splitting element and whose position is changed by a test object. The shielding unit has a region transmitting X-rays and a region having a shielding element shielding (blocking) X-rays. A dividing line between the X-ray transmitting region and the region having the shielding element is configured to be arranged obliquely so as to cross the linearly split X-ray beam.

12 Claims, 9 Drawing Sheets

(51) Int. Cl.
- *A61B 6/06* (2006.01)
- *G01N 23/04* (2006.01)
- *G21K 1/06* (2006.01)
- *A61B 6/03* (2006.01)

(56) References Cited

U.S. PATENT DOCUMENTS

| | | | |
|---|---|---|---|
| 7,535,506 B2 | 5/2009 | Nomura et al. | 348/308 |
| 7,778,389 B2 | 8/2010 | Yoneyama | 378/70 |
| 7,889,838 B2 | 2/2011 | David et al. | 378/36 |
| 8,036,336 B2 | 10/2011 | Mukaide et al. | 378/53 |
| 2009/0092227 A1* | 4/2009 | David et al. | 378/36 |
| 2011/0158389 A1 | 6/2011 | Mukaide et al. | 378/62 |
| 2011/0194674 A1 | 8/2011 | Mukaide et al. | 378/62 |

FOREIGN PATENT DOCUMENTS

| | | |
|---|---|---|
| GB | 2 441 578 A | 3/2008 |
| JP | S50-113250 | 9/1975 |
| JP | S56-161506 | 5/1981 |
| JP | S61-051506 | 3/1986 |
| WO | 2008/029107 A2 | 3/2008 |
| WO | 2009/115966 A1 | 9/2009 |

OTHER PUBLICATIONS

JPO Office Action issued on Aug. 26, 2014 in Appeal examination of counterpart Japanese patent application 2010-114477, with translation.

* cited by examiner

X-RAY IMAGING APPARATUS AND X-RAY IMAGING METHOD

RELATED APPLICATIONS

The present application is a divisional of application Ser. No. 13/125,877, filed Apr. 25, 2011, which is a National Stage filing under 35 U.S.C. §371 of International Application No. PCT/JP2010/060151, filed Jun. 9, 2010. The present application claims benefit of parent application Ser. No. 13/125,877 (PCT/JP2010/060151) under 35 U.S.C. §120, and claims priority benefit under 35 U.S.C. §119 of Japanese Patent Application 2009-145511, filed Jun. 18, 2009. The entire contents of each of the mentioned prior applications are incorporated herein by reference.

TECHNICAL FIELD

The present invention relates to an imaging apparatus and an imaging method using X-rays.

BACKGROUND ART

A nondestructive testing method using radiation has been applied to a wide range of field from an industrial application to a medical application. For example, there is an absorption contrast method using a difference in transmittance when an X-ray is transmitted through a test object. This method has been used as an application in a security field such as an internal crack inspection of an iron and steel material and a baggage inspection, using the height of the X-ray transmission capability in an absorption image obtained by the method.

Meanwhile, when the test object is made of substances having too small density difference to detect a change in contrast by X-ray absorption, X-ray phase contrast imaging for detecting a change in phase of X-rays in the test object is effective. Several of such methods have been proposed.

As one of the methods, International Publication No. WO2008/029107 discloses an imaging apparatus which provides a mask for shielding an X-ray in an edge portion of a pixel of a detector. In the absence of a test object, when setting is performed in such a manner that an X-ray is emitted to a part of the shielding mask, an X-ray positional change caused by a refraction effect of the test object can be sensed as an intensity change.

FIGS. 10A and 10B each illustrate an enlarged view of a detector portion disclosed in International Publication No. WO2008/029107. FIG. 10A is a view of the detector viewed from an X-ray incident direction, and FIG. 10B is a view of the detector viewed from a direction perpendicular to the X-ray incident direction.

A mask 1002 for shielding an X-ray is arranged in an edge portion of a pixel 1001 of the detector. An incident X-ray 1003 is incident on each pixel so as to enter a part of the mask 1002. When an X-ray is incident on a test object in such an arrangement, the position of each incident X-ray 1003 on the pixel 1001 is changed due to a refraction effect. This positional change causes the quantity of an X-ray shielded by the mask 1002 to be changed. For this reason, the refraction effect can be measured by detecting the X-ray intensity change.

DISCLOSURE OF THE INVENTION

Unfortunately, the method disclosed in International Publication No. WO2008/029107 cannot detect an X-ray intensity change with respect to an X-ray positional change if the irradiation area of the incident X-ray 1003 enters the mask 1002 or if the irradiation area thereof enters the pixel 1001 of the detector. In other words, the method disclosed in International Publication No. WO2008/029107 has a limitation in that there is an undetectable region.

In view of the above, an object of the present invention is to provide an X-ray imaging apparatus and an X-ray imaging method having less undetectable region than the method disclosed in International Publication No. WO2008/029107.

In order to achieve the above object, the X-ray imaging apparatus according to the present invention including: a splitting element which spatially linearly splits an X-ray generated from an X-ray generating unit; a shielding unit which shields a part of the X-ray which is split by the splitting element and whose position is changed by a test object; and a detecting unit which detects an intensity of the X-ray transmitted through the shielding unit, wherein the shielding unit has a region transmitting an X-ray and a region having a shielding element shielding an X-ray; and a dividing line between the X-ray transmitting region and the region having the shielding element is configured to be arranged obliquely so as to cross the linearly split X-ray.

The present invention can provide an X-ray imaging apparatus and an X-ray imaging method having less undetectable region than the method disclosed in International Publication No. WO2008/029107.

DESCRIPTION OF THE EMBODIMENTS

An X-ray imaging apparatus according to an embodiment of the present invention is configured to detect an X-ray intensity change generated by an amount of X-ray positional change occurring when a spatially split linear X-ray is transmitted through a test object and to acquire X-ray phase information from the X-ray intensity change.

In order to convert a small amount of X-ray positional change due to a refraction effect of the X-ray in the test object to X-ray intensity information and detect the X-ray intensity information, a shielding unit having an X-ray transmitting region and an X-ray shielding region is provided. The X-ray transmitting region and the X-ray shielding region are provided corresponding to one pixel of an output image (e.g., one pixel of a detector). The shielding unit is configured such that a dividing line between the X-ray transmitting region and the X-ray shielding region crosses the linearly split X-ray.

Such an X-ray shielding region is fabricated, for example, using a shielding element. As will be described in a second embodiment, in order to acquire a differential phase contrast image considering X-ray absorption information (transmittance) of a test object, two kinds of shielding elements may be alternately arranged. For example, the shielding unit may be configured such that a first region having an X-ray transmitting region and an X-ray shielding region and a second region in which a change in X-ray intensity with respect to X-ray positional change occurs in a direction opposite to that of the first region are provided and the first region and the second region are arranged alternately.

As will be described in a third embodiment, in order to acquire a differential phase contrast image considering X-ray absorption information (transmittance) of a test object, further a region not having a dividing line between an X-ray transmitting region and an X-ray shielding region may be provided.

For example, the shielding unit may be configured such that a first region having an X-ray transmitting region and an X-ray shielding region and a second region having only the X-ray transmitting region are provided and the first region and the second region are arranged alternately.

Hereinafter, further specific embodiments will be described using drawings.

First Embodiment

Figure 1:
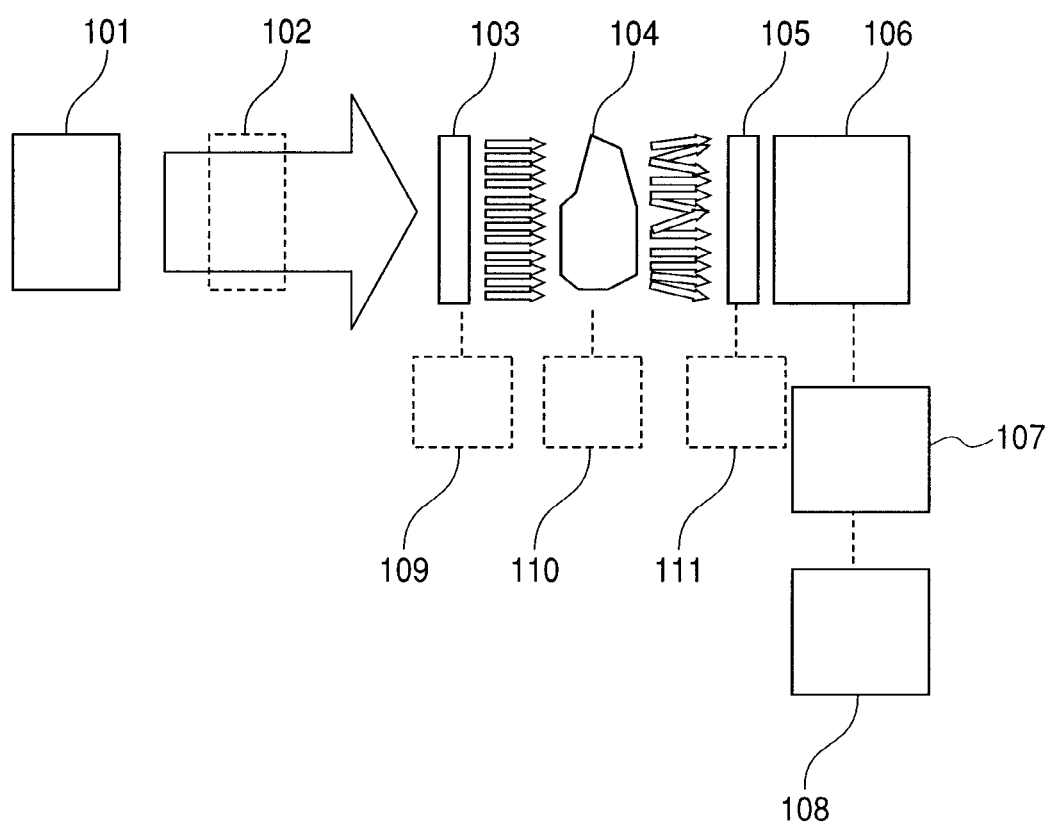
FIG. 1 is a schematic view describing a configuration of an X-ray imaging apparatus according to first, second, and third embodiments of the present invention.

Using FIG. 1, an X-ray imaging apparatus which acquires a differential phase contrast image and a phase contrast image of a test object will be described.

An X-ray generated from an X-ray source 101 as an X-ray generating unit is linearly split by a splitting element 103. The splitting element 103 is, for example, a slit array having a line-and-space pattern. Note that the splitting element 103 may be a two-dimensional slit which is split in a direction perpendicular to a slit cycle direction.

The slit provided in the splitting element 103 may be any form transmitting an X-ray and the X-ray may not pass through the splitting element substrate. The material constituting the splitting element 103 is selected from the group consisting of Pt, Au, Pb, Ta, and W having a high X-ray absorption coefficient or may be a compound containing these materials.

An X-ray split by the splitting element 103 has a line-and-space period which is equal to or greater than a pixel size of the detector 106 at a position of the detector 106. Specifically, the size of a pixel constituting an X-ray intensity detecting unit is equal to or less than a spatial period in which the X-ray split by the splitting element 103 is projected on the detecting unit.

The linear X-ray spatially split by the splitting element 103 changes its phase by a test object 104 and is refracted. Each refracted X-ray is incident on a shielding unit 105.

The intensity of each X-ray transmitted through the shielding unit 105 is detected by the detector 106. The X-ray information obtained by the detector 106 is subjected to numerical processing by a calculating unit 107, and then is output to a display unit 108 such as a monitor.

Examples of the test object 104 include a human body or as a material other than the human body, an inorganic material and an inorganic-organic composite material.

Note that moving units 109, 110, and 111 such as a stepping motor, each of which moves the splitting element 103, the test object 104, and the shielding unit 105 respectively may be provided separately.

The installation of the moving unit 110 allows the test object 104 to be moved appropriately and thus an image of a specific portion of the test object 104 can be obtained.

The detector 106 may be any X-ray detector regardless whether it is an indirect or direct type. For example, the detector 106 may be selected from an X-ray CCD camera, an indirect conversion flat panel detector, a direct conversion flat panel detector, and the like.

The detector 106 may be close to the shielding unit 105, or may be spaced at a specific distance therebetween. Alternatively, the shielding unit 105 may be built in the detector 106.

Note that when a monochromatic X-ray is used, a monochromating unit 102 may be arranged between the X-ray source 101 and the splitting element 103. The monochromating unit 102 may be a monochrometer combined with a slit or an X-ray multilayer mirror. In order to reduce image obscuration caused by a scattered X-ray from the test object 104, a grid used for X-ray photographing may be arranged between the test object 104 and the shielding unit 105.

Figure 2A:
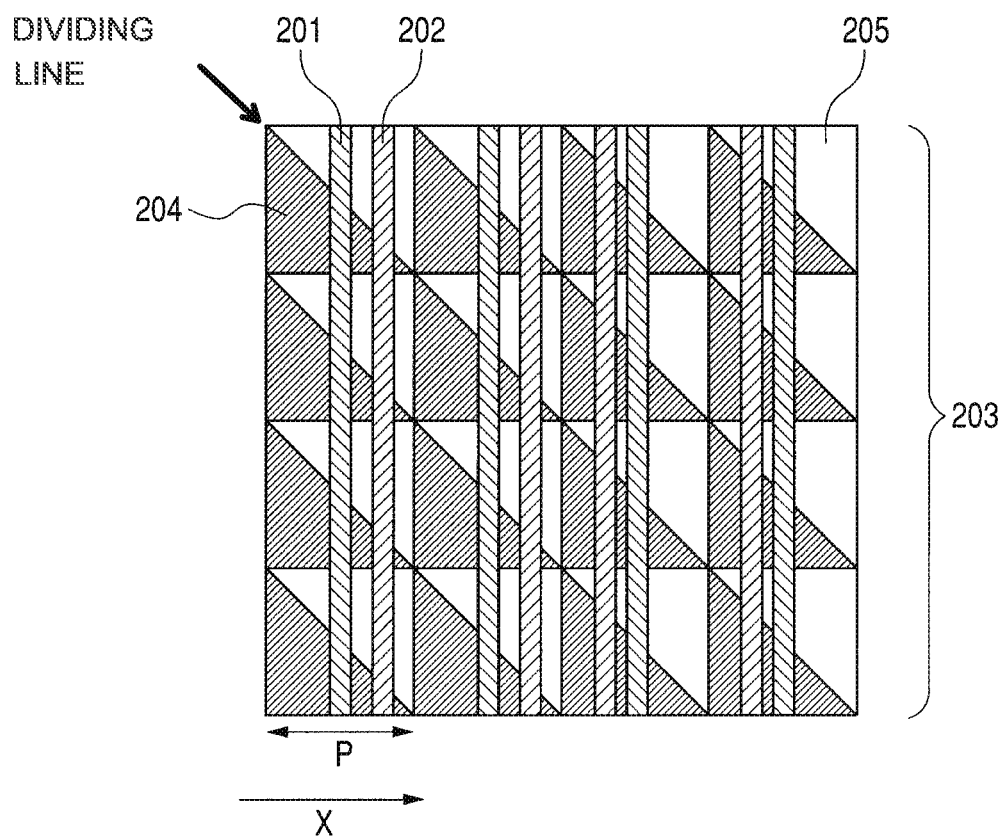
FIGS. 2A and 2B each are a schematic view describing a configuration of a shielding unit according to the first embodiment of the present invention.

Now, using FIG. 2, the shielding unit according to the present embodiment will be further described. The shielding unit 203 illustrated in FIG. 2A is a schematic view of a part of the shielding unit 105 described above in FIG. 1. A reference X-ray 201 indicates an X-ray split in the absence of the test object 104 and is incident on the pixel 205 so as to pass through the center thereof. An X-ray 202 indicates an X-ray refracted by the test object 104.

The shielding unit 203 uses the shielding element 204 to shield a part of the reference X-ray 201 in a traverse manner, the shielding region and the transmissive region thus being divided by the illustrated dividing line. When the X-ray 202 moves in an X direction with respect to the reference X-ray 201, the shape of the shielding element 204 allows the shield area of the X-ray 202 to be changed continuously. Therefore, the amount of movement can be obtained from the change in intensity.

The method disclosed in International Publication No. WO2008/029107 cannot obtain the amount of X-ray positional change when the X-ray enters a mask. On the contrary to this, the configuration illustrated in FIG. 2A can reduce the undetectable region in comparison with the method disclosed in International Publication No. WO2008/029107.

When the shielding unit 203 as illustrated in FIG. 2A is used and a reference X-ray 201 is incident on the pixel 205 so as to pass through the center thereof, the intensity (I) of the reference X-ray 201 detected by the detector 106 is expressed by expression (1).

$$I = \frac{1}{2} I_0 \qquad \text{Expression (1)}$$

Here, $I_0$ is the intensity of an X-ray which is spatially split by the splitting element 103 and enters the pixel 205.

Meanwhile, when the X-ray 202 is refracted by the test object 104 and moves by $\Delta x$ in the X direction, the detection intensity (I') of the X-ray 202 is expressed by expression (2).

$$I' = I_0\left(\frac{1}{2} + \frac{\Delta x}{P}\right) \quad \text{Expression (2)}$$

Here, P is the size of one side of the pixel 205.

From the expression (2), the line width of the reference X-ray 201 has no relationship to the X-ray intensity change with respect to the amount of X-ray movement. In addition, the line width of the reference X-ray 201 has no relationship to the X-ray intensity change ratio with respect to the amount of X-ray movement. In other words, the movement detection width can be enlarged simply by narrowing the width of the reference X-ray 201. From the expression (1) and the expression (2), the amount of positional change ($\Delta x$) from the reference X-ray 201 to the X-ray 202 is expressed by expression (3).

$$\Delta x = \frac{P(I' - I)}{2I} \quad \text{Expression (3)}$$

Figure 3:
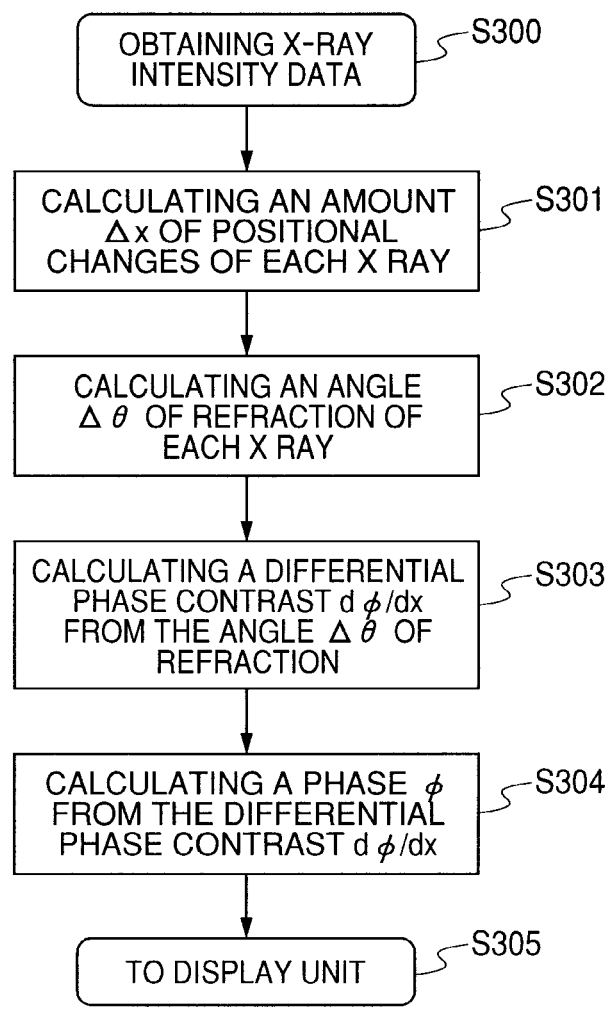
FIG. 3 is a flowchart describing a calculating method according to the first embodiment of the present invention.

FIG. 3 is a flowchart of the calculation processing.

First, intensity data of each X-ray is acquired (S300).

Then, from the X-ray intensity of each pixel 205, the amount of positional change ($\Delta x$) with respect to the reference X-ray 201 is calculated (S301).

Alternatively, the amount of positional change ($\Delta x$) may be obtained in such a manner that the corresponding relation between an X-ray intensity detected in the absence of the test object 104 and an X-ray position (x) is stored as a data table in the calculating unit 107 or other memory, and a measured intensity is used to refer to the data table to obtain the amount of positional change ($\Delta x$).

This data table can be made by moving the splitting element 103 for each shielding element 204 and detecting the intensity of an X-ray transmitted at each position of the shielding element 204.

Alternatively, the data table can also be made by moving an element having a single slit with the same width as the slit width of the splitting element 103 instead of the splitting element 103 and detecting the intensity of an X-ray transmitted at each position of the shielding element 204.

Then, a refraction angle ($\Delta\theta$) of each X-ray is calculated using the following expression (4) (S302).

$$\Delta\theta = \tan^{-1}\left(\frac{\Delta x}{Z}\right) \quad \text{Expression (4)}$$

Here, $\Delta x$ refers to the amount of positional change and Z refers to the distance between the test object 104 and the shielding unit 105.

Then, the X-ray differential phase ($d\phi/dx$) of each pixel 205 is calculated using the following expression (5) (S303).

$$\frac{d\phi}{dx} = \frac{2\pi}{\lambda}\Delta\theta \quad \text{Expression (5)}$$

Here, $\lambda$, is an X-ray wavelength and, when a continuous X-ray is used, $\lambda$, refers to an effective wavelength. Then, the phase ($\phi$) is calculated by integrating each of the obtained differential phases ($d\phi/dx$) in the X direction (S304).

The display unit 108 can display the differential phase contrast image and the phase contrast image calculated in this manner as well as a measured intensity distribution image (S305).

According to the above configuration, the width of the reference X-ray 201 has no relationship to the X-ray intensity change ratio with respect to the amount of X-ray positional change, and thus the range of detecting the amount of positional change can be freely adjusted. For this reason, imaging can range from a region of a large phase gradient to a region of a small phase gradient in an easy manner.

Unfortunately, the method disclosed in International Publication No. WO2008/029107 cannot detect an X-ray intensity change with respect to an X-ray positional change if the irradiation area of the incident X-ray enters the mask or if the irradiation area thereof enters a pixel of the detector. Therefore, according to the method disclosed in International Publication No. WO2008/029107, the detectable movement width is determined by the incident X-ray width. On the contrary, as described above, the present embodiment has an advantage that the detectable movement width is not determined by the incident X-ray width.

Figure 2B:
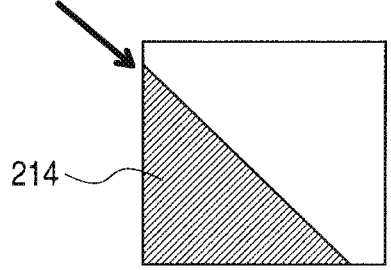

Note that the shielding element is not limited to a configuration in which corners of a pixel are connected to each other as illustrated in FIG. 2A, but the shielding element 214 may be configured as illustrated in FIG. 2B. Even the above configuration can reduce the undetectable region than the method disclosed in International Publication No. WO2008/029107.

Second Embodiment

The second embodiment illustrates an example of an X-ray imaging apparatus and an imaging method which can be suitably used for a case in which the test object can sufficiently absorb an X-ray. Specifically, when the test object absorbs an X-ray, the first embodiment cannot determine whether the X-ray intensity change is caused by absorption by the test object or X-ray positional change.

Figure 4:
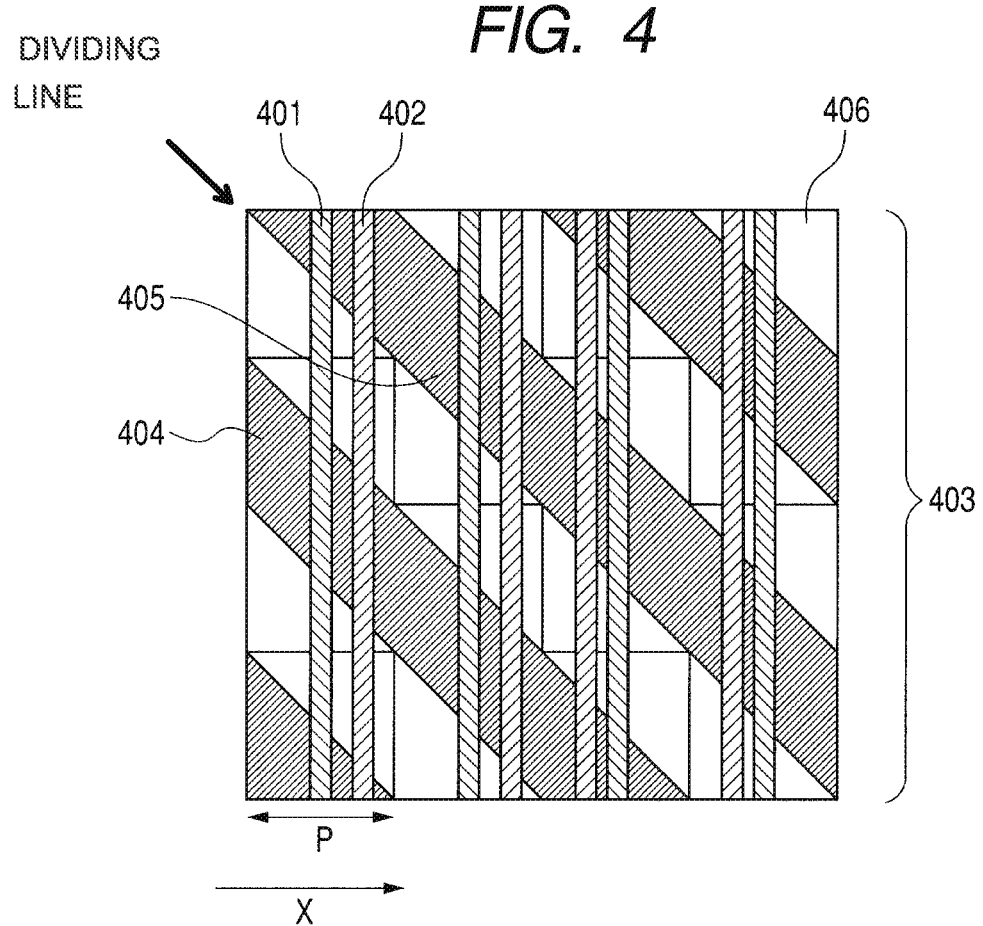
FIG. 4 is a schematic view describing a configuration of a shielding unit according to a second embodiment of the present invention.

In light of this, the present embodiment uses a shielding unit illustrated in FIG. 4 instead of the shielding unit described in the first embodiment. Specifically, the present embodiment uses a shielding unit in which the shape of an X-ray shielding element is different between adjacent pixels.

The apparatus configuration other than the above is the same as that of the first embodiment, and thus using FIG. 4, the shielding unit according to the present embodiment will be described.

The shielding unit 403 illustrated in FIG. 4 is a schematic view of a part of the shielding unit 105 described above in FIG. 1. A reference X-ray 401 refers to an X-ray split in the absence of the test object 104 and can be incident on the center of the pixel 406 in the X direction. An X-ray 402 refers to an X-ray refracted by the test object 104. A shielding unit 403 is configured such that a shielding element 404 (first shielding element) and a shielding element 405 (second shielding element) are alternately arranged. The shielding element 404 (first shielding element) is a structure in which the incident X-ray intensity becomes stronger with the movement in the X direction. On the contrary, the shielding element 405 (second shielding element) is a structure in which the incident X-ray intensity becomes weaker with the movement in the X direction. In other words, both shielding elements have an opposite relationship between the amount of X-ray detection and the X-ray movement direction.

The X-ray intensity ($I'_1$) obtained through the test object 104 and the shielding element 404 is expressed by the following expression (6).

$$I'_1 = AI_{01}\left(\frac{1}{2} + \frac{\Delta x}{P}\right) \quad \text{Expression (6)}$$

The $I_{01}$ is the intensity of an X-ray which is spatially split by the splitting element 103 in the absence of the test object 104 and enters the center of each pixel 406 in the X direction, and P is the size of one side of the pixel 406. A is an X-ray transmittance of the test object 104.

Meanwhile, the X-ray intensity ($I'_2$) obtained through the test object 104 and the shielding element 405 is expressed by the following expression (7).

$$I'_2 = AI_{02}\left(\frac{1}{2} - \frac{\Delta x}{P}\right) \quad \text{Expression (7)}$$

The $I_{02}$ is the intensity of an X-ray which is spatially split by the splitting element 103 in the absence of the test object 104 and enters the center of each pixel 406 in the X direction.

Assuming that the detection intensity of the reference X-ray 401 with respect to the shielding elements 404 and 405 is $I_1$ and $I_2$ respectively, from the expression (6) and the expression (7), the amount of positional change ($\Delta x$) can be expressed by the following expression (8).

$$\Delta x = \frac{P(I'_1 I_2 - I_1 I'_2)}{2(I_1 I'_2 + I'_1 I_2)} \quad \text{Expression (8)}$$

In this manner, $\Delta x$ can be obtained by the expression (8). Thus, the X-ray transmittance (A) of the test object 104 can be obtained using $\Delta x$.

Alternatively, even if the reference X-ray 401 does not enter the center of the pixel 406, the corresponding relation between an X-ray intensity detected in the absence of the test object 104 and an X-ray position (x) within the pixel 406 may be stored as a data table in the calculating unit 107 or other memory. Then, the amount of positional change ($\Delta x$) and the X-ray transmittance (A) may be calculated. Specifically, according to the above data table, the position (x) of the reference X-ray 401 in the absence of the test object 104 can be known. Therefore, the amount of positional change ($\Delta x$) and the X-ray transmittance (A) can be calculated by associating the expression (6), the expression (7), and the expression (8) with the position (x) of the reference X-ray 401.

This data table can be made by moving the splitting element 103 for each of shielding elements 404 and 405 and detecting the intensity of an X-ray transmitted at each position of the shielding elements 404 and 405. Alternatively, the data table can also be made by moving an element having a single slit with the same width as the slit width of the splitting element 103 instead of the splitting element 103 and detecting the intensity of an X-ray transmitted at each position of the shielding elements 404 and 405.

In other words, from the relationship between the detection intensities of the reference X-ray 401 and the X-ray 402 in the adjacent shielding elements 404 and 405, the transmittance due to an absorption effect of the test object 104 and the amount of positional change due to refraction can be obtained.

Note that in this case, X-ray intensity information in the two regions of the shielding element 404 and the shielding element 405 is used, and thus the spatial resolution in the X direction becomes ½.

In light of this, in addition to the above measurement, a measurement can be made likewise by moving the shielding unit 105 or the test object 104 in the X direction for the length of the shielding element 404 in the X direction by a moving unit 111 or a moving unit 110, respectively.

By doing this, information about the X-ray transmittance (A) and the amount of positional change ($\Delta x$) corresponding to the position of the test object 104 in which the amount of X-ray positional change is measured before can be obtained.

The X-ray passed through the shielding unit 105 is detected by the X-ray detector 106, and the calculating unit 107 can be used to calculate the transmittance (A), the differential phase ($d\phi/dx$), and the phase ($\phi$). In addition, thus calculated transmittance image, differential phase contrast image, and phase contrast image can also be displayed on the display unit 108.

Figure 5:
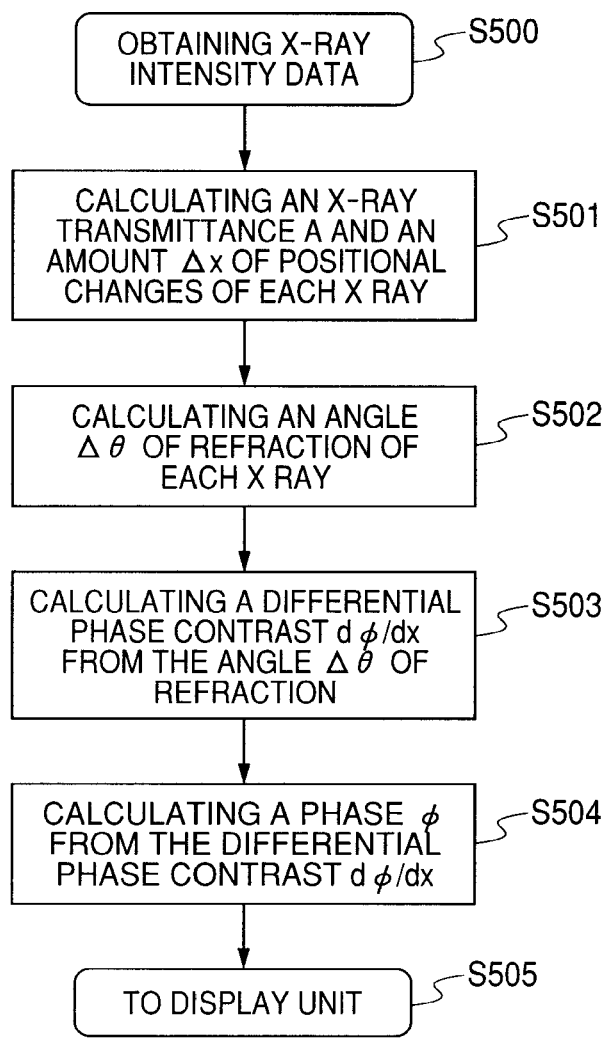
FIG. 5 is a flowchart describing a calculating method according to the second embodiment of the present invention.

Then, using FIG. 5, the calculation processing flow will be described.

First, intensity information on each X-ray is acquired (S500).

Then, from each X-ray intensity, the amount of positional change ($\Delta x$) with respect to the reference X-ray 401 and the X-ray transmittance (A) are calculated (S501).

Then, in the same manner as in the first embodiment, the refraction angle ($\Delta\theta$) of each X-ray is calculated using the amount of positional change ($\Delta x$) and the distance (Z) between the test object 104 and the shielding unit (X-ray attenuation unit) 105 (S502). From the refraction angle ($\Delta\theta$) of each X-ray, the differential phase ($d\phi/dx$) is calculated (S503). Then, the phase ($\phi$) is calculated by integrating each of the obtained differential phases ($d\phi/dx$) in the X direction (S504).

The transmittance image, the differential phase contrast image, and the phase contrast image calculated in this manner can be displayed by the display unit 108 (S505). In addition, the measured intensity distribution image can also be displayed.

Third Embodiment

The third embodiment illustrates an example of an X-ray imaging apparatus and an imaging method which can be suitably used for a case in which the test object can sufficiently absorb an X-ray.

Figure 6:
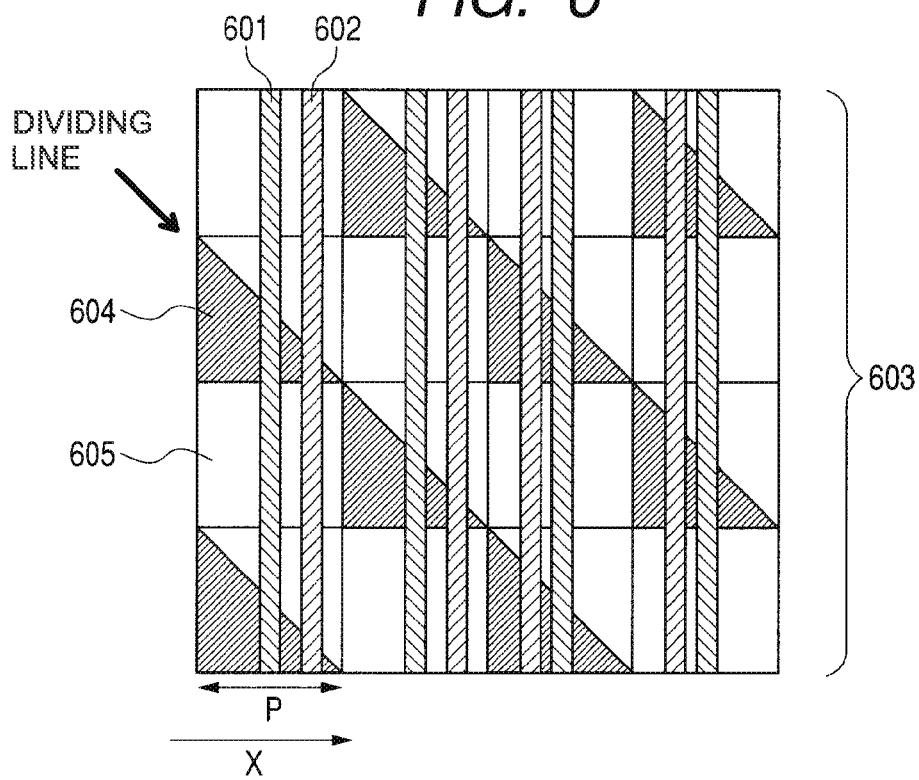
FIG. 6 is a schematic view describing a configuration of a shielding unit according to a third embodiment of the present invention.

The present embodiment is different from the first embodiment in that the shielding unit illustrated in FIG. 6 is used instead of the shielding unit described in the first embodiment. Specifically, the present embodiment provides a region having an X-ray shielding portion and a region not having an X-ray shielding portion.

The basic apparatus configuration other than the above is the same as that of the first embodiment, and thus using FIG. 6, the shielding unit according to the present embodiment will be described.

A reference X-ray 601 refers to an X-ray split in the absence of the test object 104 and can be incident on the center of the shielding element 604 in the X direction. An X-ray 602 refers to an X-ray refracted by the test object 104. A shielding unit 603 is configured such that a region having a shielding element 604 and a region 605 in which the X-ray intensity does not change with respect to an X-ray movement are alternately arranged.

According to the above configuration, from the region 605 not having the shielding element 604, the X-ray transmittance A of the test object 104 can be calculated; and from the transmittance A of each region 605 not having the shielding element 604, the transmittance of the region having the shielding element 604 can be calculated in a complementary manner.

In addition, the refraction angle of the X-ray 602 in each region having the shielding element 604 can be calculated and thus in the same manner as in the transmittance A, the refraction angle in each region 605 not having the shielding element 604 can be calculated in a complementary manner.

Note that in this case, X-ray intensity information in the two different regions of the region having the shielding element 604 and the region 605 not having the shielding element 604 is used, and thus the spatial resolution in the X direction becomes ½. Regarding this problem, the spatial resolution can be improved by moving the shielding unit 603 by one pixel in the X direction and taking another image. Specifically, information about the X-ray transmittance (A) corresponding to the position of the test object 104 in which the amount of X-ray positional change is measured before and the refraction angle thereof can be obtained. Alternatively, the test object 104 may be moved by a distance of one period of the X-ray split by the splitting element 103 and another image may be taken.

Figure 7:
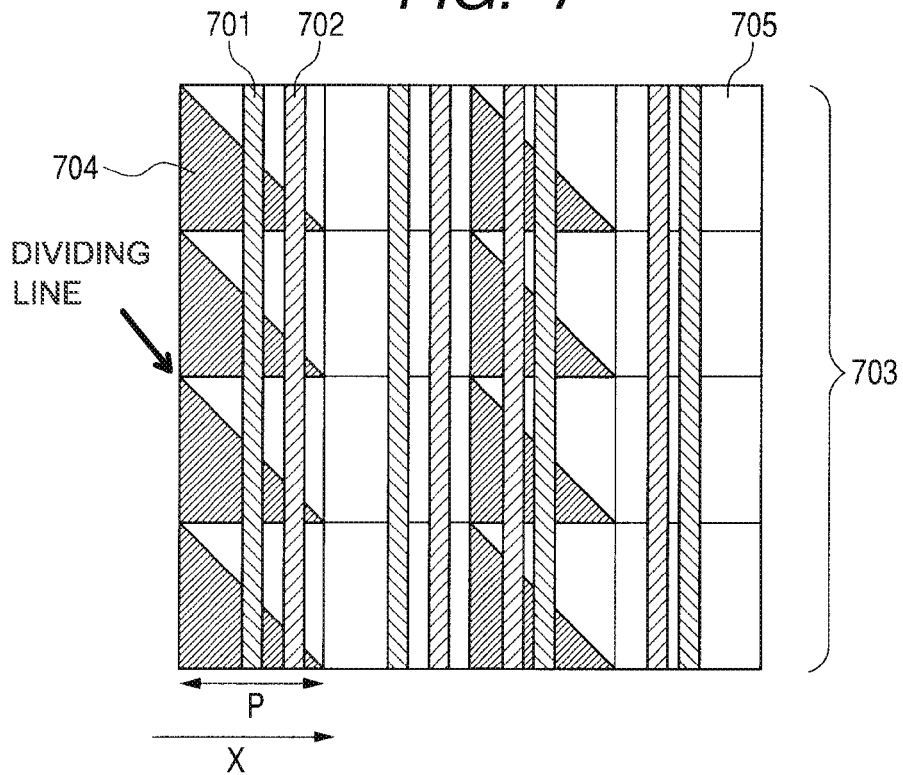
FIG. 7 is a schematic view describing a configuration of a shielding unit according to a third embodiment of the present invention.

Further, the spatial resolution may be improved by using a shielding unit as illustrated in FIG. 7.

In FIG. 7, a reference X-ray 701 refers to an X-ray split in the absence of the test object 104. The reference X-ray 701 can be incident on the center of the shielding element 704 in the X direction. An X-ray 702 refers to an X-ray refracted by the test object 104. The shielding unit 703 is configured such that a shielding element 704, which is a structure in which the X-ray intensity changes with the movement in the X direction, forms a row, and a region 705 in the adjacent row, in which the X-ray intensity does not change with the movement in the X direction and which does not have the shielding element 704, is alternately arranged.

This shielding unit 703 is used to take two images, one in the absence of the test object 104 and one in the presence thereof, and further the shielding unit 703 is moved by one pixel in the X direction and another two images are taken. Alternatively, the test object 104 may be moved by a distance of one period of the X-ray split by the splitting element 103 and another image may be taken.

Thereby, information about the X-ray transmittance (A) corresponding to the position of the test object 104 in which the amount of X-ray positional change is measured before and the refraction angle can be obtained.

The flowchart of the calculation processing 107 is the same as that of the second embodiment.

According to the above configuration, the differential phase contrast image and the phase contrast image considering the absorption effect can be measured.

Example

Figure 8:
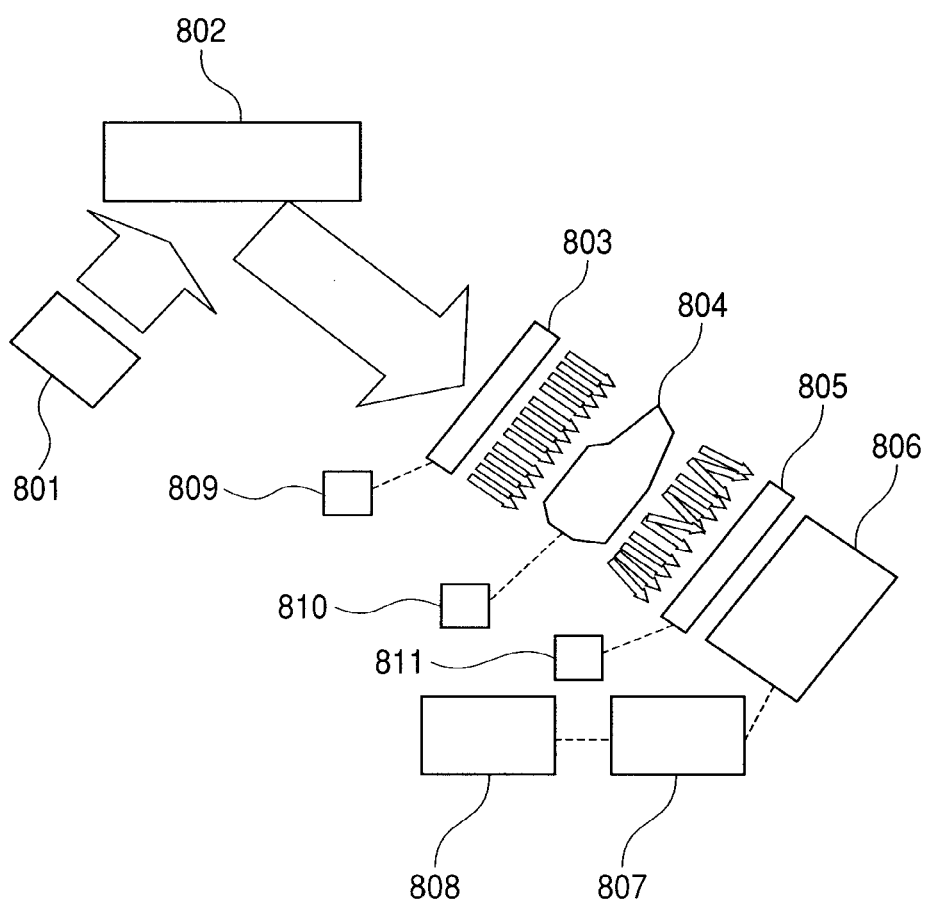
FIG. 8 is a schematic view describing a configuration of the X-ray imaging apparatus according to an Example of the present invention.

Using FIG. 8, the X-ray imaging apparatus according to an embodiment of the present invention will be described. As the X-ray generating unit, a rotating-anode-type X-ray generator having a Mo target illustrated in an X-ray source 801 is used.

As an X-ray monochromating unit 802, a highly oriented pyrolytic graphite (HOPG) monochrometer and a multilayer minor are used to extract an X-ray portion having Mo characteristic X-ray.

The X-ray monochromatized by the monochromating unit 802 is spatially split by the splitting element 803 arranged in a position spaced 100 cm from the X-ray source. As the splitting element 803, W with a thickness of 100 μm and a slit with a width of 40 μm arranged thereon are used. The slit period is about 150 μm on the shielding unit 805. Note that as the material, not only W but also Au, Pb, Ta, and Pt can be used.

The X-ray split by the splitting element 803 is emitted to the test object 804.

The X-ray transmitted through the test object 804 is incident on the shielding unit 805 located at a position spaced about 50 cm from the test object 804.

Note that moving units 809, 810, and 811 each using a stepping motor are provided in the splitting element 803, the test object 804, and the shielding unit 805 respectively.

Figure 9:
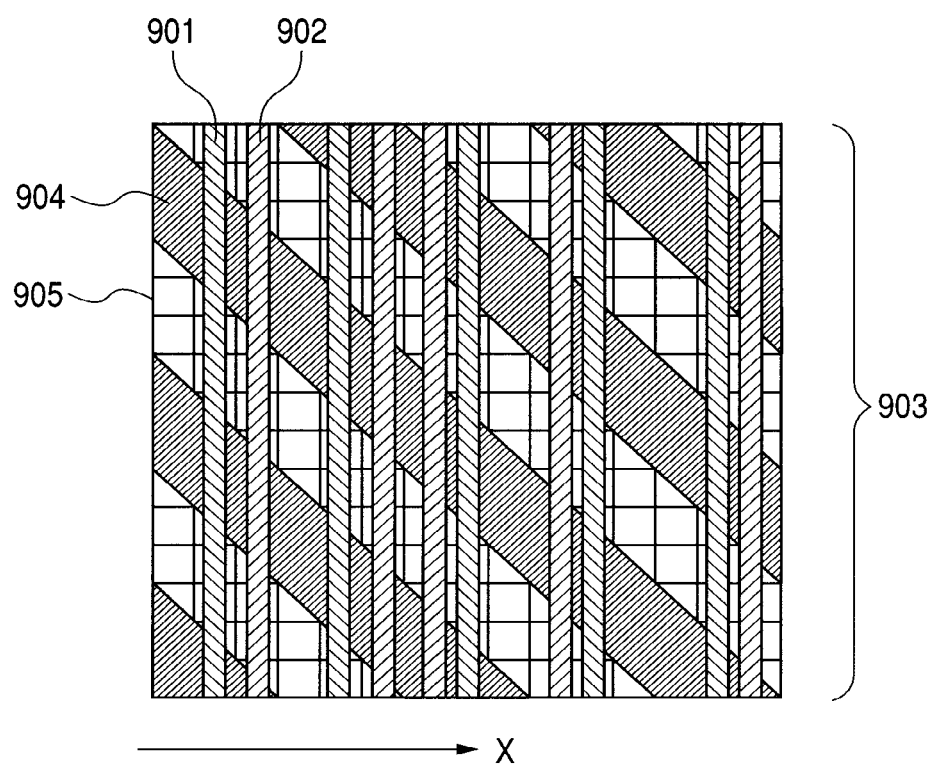
FIG. 9 is a schematic view describing a configuration of a shielding unit according to an Example of the present invention.
Figure 10A:
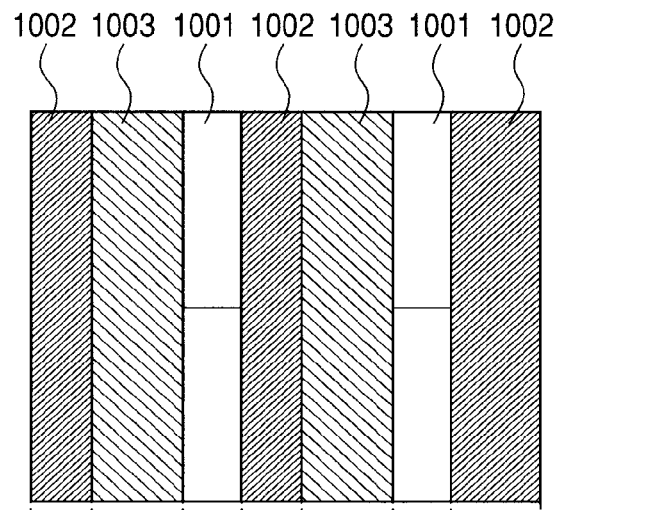
FIGS. 10A and 10B each are a schematic view describing a configuration of an X-ray imaging apparatus according to a conventional example disclosed in International Publication No. WO2008/029107.
Figure 10B:
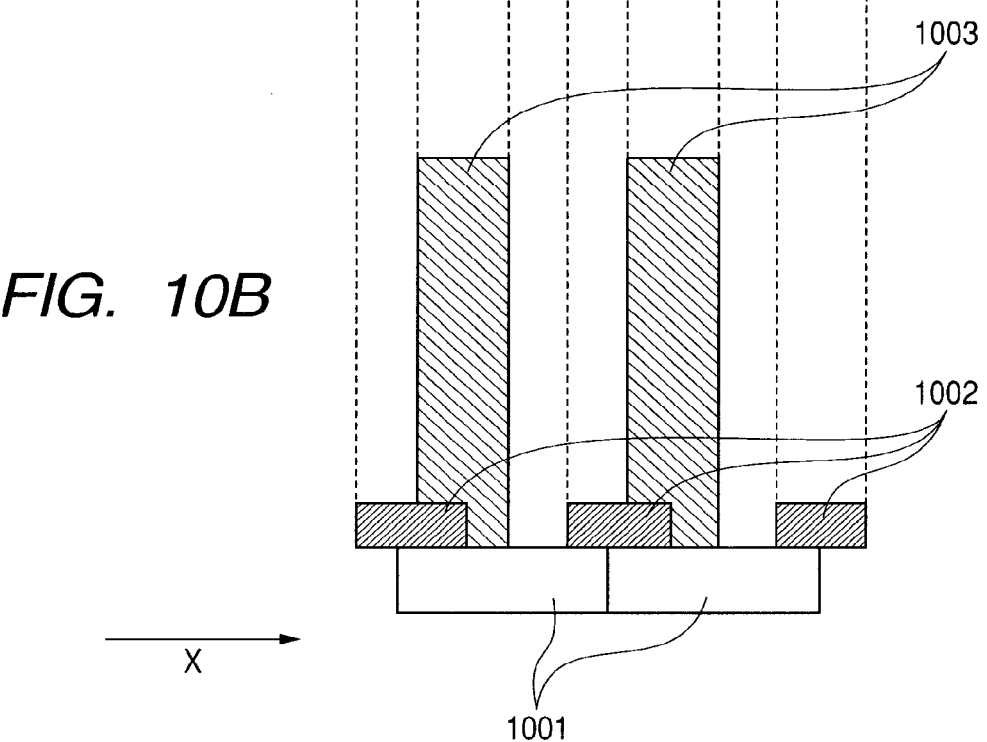

Using FIG. 9, the shielding unit 805 according to the present embodiment will be described.

A shielding element 904 having a shielding region with a width of about 105 μm and a period of about 212 μm is formed on W with a thickness of 100 μm. This is used as a shielding unit 903 and is arranged so as to have periodicity in an oblique 45° direction with respect to a pixel of the X-ray detector 806.

An X-ray detector 806 as the detecting unit arranged immediately after the shielding unit 805 detects the intensity of the reference X-ray 901 transmitted through the shielding unit 805 and the X-ray 902 refracted by the test object 804. The reference X-ray 901 enters the center of each period with respect to the lateral 3-pixel period of the X-ray detector 806.

Subsequently, the moving unit 811 is used to move the shielding unit 805 by 150 μm in the X direction and then perform a similar measurement.

The X-ray detector 806 uses a flat panel detector with a pixel 905 sized about 50 μm×50 μm, the X-ray intensity values of a 3×3 pixels square are added to produce one pixel of information on an output image.

From a change in intensity of each X-ray when a similar imaging is performed in the absence of the test object 804, the calculating unit 807 calculates the X-ray transmittance (A) of each X-ray in the test object 804 to obtain an absorption image.

Then, the amount of positional change ($\Delta x$) is calculated by the expression (8) and the refraction angle ($\Delta \theta$) is calculated by the expression (4). In this case, the size of three pixels is used as the value of P in the expression (8).

From the refraction angle ($\Delta \theta$), the amount of differential phase is calculated by the expression (5). A phase distribution image is calculated by spatially integrating the amount of differential phase obtained from each X-ray.

The X-ray transmittance image, the X-ray differential phase contrast image, and the X-ray phase contrast image obtained by the calculating unit 807 are displayed on a PC monitor as the display unit 808.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The invention claimed is:

1. An X-ray imaging apparatus comprising:
   a shielding unit which blocks an X-ray which is a part of an X-ray beam; and
   a detecting unit which has a plurality of pixels and detects an intensity of an X-ray which is a part of the X-ray beam and which is transmitted through said shielding unit,
   wherein said shielding unit blocks a part of the X-ray of which an incident position at said shielding unit is changed by an object,
   wherein said shielding unit has an X-ray transmitting region and a plurality of X-ray shielding regions arranged so as to form a dividing line between said X-ray transmitting region and said X-ray shielding regions such that the dividing line crosses the X-ray beam and is configured to be arranged so as to monotonically increase or decrease the intensity of the X-ray which is detected by at least a part of said pixels as an incident position of the X-ray beam at said shielding unit is changed to a first direction, and wherein said plurality of X-ray shielding regions are arranged in a period which is equal to or greater than a pixel arrangement period at a position of said detecting unit.

2. The X-ray imaging apparatus according to claim 1, further comprising a calculating unit which calculates one of an X-ray transmittance image, a differential phase contrast image, and a phase contrast image of the test object from an X-ray intensity change detected by said detecting unit.

3. The X-ray imaging apparatus according to claim 1, wherein a width of the X-ray beam is smaller than the width of at least one of said shielding regions.

4. The X-ray imaging apparatus according to claim 1, wherein said shielding unit has a first region having a first X-ray transmitting region and a first X-ray shielding region, and a second region having a second X-ray transmitting region, wherein said first region and said second region are arranged alternately, and wherein, in said first region, an incident position of the X-ray beam to said shielding unit is configured to be arranged so as to monotonically increase or decrease the intensity of the X-ray which is detected by at least a part of said pixels as the incident position is changed to the first direction.

5. The X-ray imaging apparatus according to claim 1, wherein said shielding unit has a first region having a first X-ray transmitting region and a first X-ray shielding region, and a second region having a second X-ray transmitting region and a second X-ray shielding region, a change in X-ray intensity in the second region occurring in a direction opposite to a change in X-ray intensity in the first region, said first region and said second region being arranged alternately, wherein, in said second region, a dividing line between said second X-ray transmitting region and said second X-ray shielding region is configured to be arranged so as to cross the X-ray beam which enters said second region, wherein, in said first region, an incident position of the X-ray beam at said shielding unit is configured to be arranged so as to monotonically increase the intensity of the X-ray which is detected by at least a part of said pixels as the incident position is changed to the first direction, and wherein, in said second region, an incident position of the X-ray beam at said shielding unit is configured to be arranged so as to monotonically decrease the intensity of the X-ray which is detected by at least a part of said pixels as the incident position is changed to the first direction.

6. The X-ray imaging apparatus according to claim 1, wherein said X-ray transmitting region and said X-ray shielding regions are arranged so as to form a dividing line which crosses a contour of the X-ray beam.

7. The X-ray imaging apparatus according to claim 1, further comprising a splitting element having an X-ray transmitting region and an X-ray shielding region, wherein the X-ray beam is formed by said splitting element, and wherein a projection image of the splitting element is formed on said shielding unit.

8. The X-ray imaging apparatus according to claim 4, further comprising a splitting element having an X-ray transmitting region and an X-ray shielding region, wherein the X-ray beam is formed by said splitting element, and wherein a projection image of the splitting element is formed on said shielding unit.

9. The X-ray imaging apparatus according to claim 5, further comprising a splitting element having an X-ray transmitting region and an X-ray shielding region, wherein the X-ray beam is formed by said splitting element, and wherein a projection image of the splitting element is formed on said shielding unit.

10. The X-ray imaging apparatus according to claim 4, wherein said first X-ray shielding region is arranged in a period which is equal to or greater than a pixel arrangement period at a position of said detecting unit.

11. The X-ray imaging apparatus according to claim 5, wherein said first and second X-ray shielding region are each arranged in a period which is equal to or greater than a pixel arrangement period at a position of said detecting unit.

12. The X-ray imaging apparatus according to claim 1, further comprising a calculating unit which calculates an amount of positional change of X-ray beam caused by a test object from an X-ray intensity of each pixel.

* * * * *